(12) United States Patent
Helmer (10) Patent No.: US 10,549,039 B2
(45) Date of Patent: Feb. 4, 2020

(54) DRUG DELIVERY DEVICE

(71) Applicant: SANOFI-AVENTIS DEUTSCHLAND GMBH, Frankfurt am Main (DE)

(72) Inventor: Michael Helmer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 170 days.

(21) Appl. No.: 15/736,627

(22) PCT Filed: Jun. 15, 2016

(86) PCT No.: PCT/EP2016/063697
§ 371 (c)(1),
(2) Date: Dec. 14, 2017

(87) PCT Pub. No.: WO2016/202829
PCT Pub. Date: Dec. 22, 2016

(65) Prior Publication Data
US 2018/0185585 A1     Jul. 5, 2018

(30) Foreign Application Priority Data
Jun. 18, 2015 (EP) .................................... 15172769

(51) Int. Cl.
*A61M 5/24* (2006.01)
*A61M 5/32* (2006.01)
*A61M 5/28* (2006.01)

(52) U.S. Cl.
CPC ........ *A61M 5/2466* (2013.01); *A61M 5/3202* (2013.01); *A61M 5/288* (2013.01);
(Continued)

(58) Field of Classification Search
CPC .............. A61M 5/2466; A61M 5/2455; A61M 5/3202; A61M 2005/3267; A61M 5/288; A61M 2005/2474
See application file for complete search history.

(56) References Cited

U.S. PATENT DOCUMENTS 3,825,003 A * 7/1974 Kruck .................. A61M 5/288
                                                                                        604/192
4,976,701 A     12/1990 Ejlersen et al.
(Continued)

FOREIGN PATENT DOCUMENTS

EP             3106190        12/2016
WO    WO 2007/131013      11/2007
(Continued)

OTHER PUBLICATIONS

International Search Report and Written Opinion in International Application No. PCT/EP2016/063697, dated Aug. 29, 2016, 15 pages.
(Continued)

*Primary Examiner* — Bradley J Osinski
(74) *Attorney, Agent, or Firm* — Fish & Richardson P.C.

(57) ABSTRACT

The disclosure relates to a drug delivery device, comprising: an outer needle sleeve; a cartridge containing a dosage of a medicament and sealed with a sealing element that is arranged across an open distal end of the cartridge; a cartridge carrier adapted to hold the cartridge; a needle hub adapted to hold a double ended hollow needle; an inner needle sleeve arranged between the needle hub and the cartridge carrier; a removable cap coupled to the inner needle sleeve and adapted to cover and seal the needle; and a first locking mechanism adapted to lock the inner needle sleeve against axial movement in the proximal direction with respect to the cartridge carrier in an initial state, wherein in the initial state, the needle is spaced from the
(Continued)

cartridge in the distal direction, and wherein the first locking mechanism is releasable by a rotational movement of the cap with respect to the outer needle sleeve.

15 Claims, 4 Drawing Sheets

(52) U.S. Cl.
CPC ............... *A61M 2005/2474* (2013.01); *A61M 2005/3267* (2013.01); *A61M 2205/581* (2013.01); *A61M 2205/582* (2013.01)

(56) References Cited

U.S. PATENT DOCUMENTS

| | | | | |
|---|---|---|---|---|
| 5,250,037 A | * | 10/1993 | Bitdinger | A61M 5/3202 604/192 |
| 2011/0295215 A1 | * | 12/2011 | Nielsen | G16H 20/17 604/257 |

FOREIGN PATENT DOCUMENTS

| | | |
|---|---|---|
| WO | WO 2013/063707 | 5/2013 |
| WO | WO 2015/001819 | 1/2015 |

OTHER PUBLICATIONS

International Preliminary Report on Patentability in International Application No. PCT/EP2016/063697, dated Dec. 19, 2017, 11 pages.

* cited by examiner

DRUG DELIVERY DEVICE

CROSS REFERENCE TO RELATED APPLICATIONS

The present application is the U.S. national stage entry under 35 USC § 371 of International Patent Application No. PCT/EP2016/063697, filed on Jun. 15, 2016, which claims priority to European Patent Application No. 15172769.0, filed on Jun. 18, 2015, the entire contends of which are incorporated herein by reference.

TECHNICAL FIELD

The disclosure relates to a drug delivery device.

BACKGROUND

Administering an injection is a process which presents a number of risks and challenges for users and healthcare professionals, both mental and physical. Pre-filled syringes with a syringe cartridge containing a selected dosage of a medicament for administering the medicament to a patient are known in the art. The cartridges may be stored in a blistered package so that they remain sterile until the time of use. The cartridges include a hollow injection needle that is in fluid communication with the medicament stored in the cartridge. Thus, the injection needle can be clogged after a long-term storage.

SUMMARY

An improved drug delivery device is disclosed herein that is configured for reducing the risk of a clogged needle during storage.

Implementations can include one or more of the following features.

According to the disclosure, a drug delivery device comprises: an outer needle sleeve; a cartridge containing a medicament and sealed with a sealing element that is arranged across an open distal end of the cartridge; a cartridge carrier adapted to hold the cartridge; a needle hub adapted to hold a double ended hollow needle; an inner needle sleeve arranged between the needle hub and the cartridge carrier; a removable cap coupled to the inner needle sleeve and adapted to cover and seal the needle; and a first locking mechanism adapted to lock the inner needle sleeve against axial movement in the proximal direction with respect to the cartridge carrier in an initial state, wherein in the initial state the double-ended hollow needle is spaced from the cartridge in the distal direction; and wherein the first locking mechanism is releasable by a rotational movement of the cap with respect to the outer needle sleeve.

In the drug delivery device according to the disclosure, the double-ended hollow needle gets in contact with the medicament contained in the cartridge immediately before the start of a drug delivery process. Thus, the drug delivery device reduces the risk for clogging the needle by the medicament compared with the related art, whereby a time required for drug delivery will not be increased. The double-ended hollow needle can be preassembled to the drug delivery device and will remain sterile and clean until the beginning of drug delivery. Here, the initial position of the drug delivery device is a position in which the device would be presented to a user prior to use, whereby the double-ended hollow needle is not in fluid communication with the medicament stored in the cartridge. The sealing element seals the medicament stored in the cartridge against environmental influences and ensures that the medicament remains within the cartridge before starting drug delivery.

In an exemplary embodiment, an angle of the rotational movement of the cap with respect to the outer needle sleeve is in a range of 30 degrees to 45 degrees.

In an alternative embodiment, an angle of the rotational movement of the cap with respect to the outer needle sleeve is in a range of 30 degrees to 90 degrees.

In a further alternative embodiment, an angle of the rotational movement of the cap with respect to the outer needle sleeve is in more than 90 degrees.

In an exemplary embodiment, the first locking mechanism comprises a number of recesses arranged in the outer circumference of a distal portion of the cartridge carrier and a number of sleeve ribs arranged on an inner circumference of the inner needle sleeve and projecting radially inwards. Likewise, the ribs could be arranged outwardly projecting on the outer circumference of the distal portion of the cartridge carrier and the recesses could be arranged on the inner circumference of the inner needle sleeve.

When the drug delivery device is in the initial position, a distal end of the cartridge carrier couples to the sleeve ribs, wherein the recesses are angularly misaligned from the sleeve ribs. The first locking mechanism may then be released when the sleeve ribs engage into the recesses due to the rotational movement of the cap, wherein the needle hub and the needle sleeve move in the proximal direction with respect to the cartridge carrier.

When the needle hub and the inner needle sleeve move in the proximal direction with respect to the cartridge carrier, a needle tip of a proximal needle section pierces the sealing element. As a result, the needle gets in fluid communication with the medicament stored in the cartridge.

In an exemplary embodiment, the coupling of the cap and the inner needle sleeve is achieved by a plurality of sleeve pins arranged on a distal end of the inner needle sleeve and projecting axially in a distal direction and by a plurality of cap arms arranged on a distal end of the cap and projecting axially in a proximal direction. The needle hub may then comprise a plurality of openings through which the sleeve pins projects. The number of openings may correspond with a number of sleeve pins.

In an exemplary embodiment, the drug delivery device comprises a second locking mechanism adapted to lock the cap against axial removal from the outer needle sleeve. The second locking mechanism may be releasable when the first locking mechanism is released. Thus, an unintended removal of the cap is prevented before the needle has pierced the sealing element.

For example, the second locking mechanism includes a bayonet connection between the cap and the outer needle sleeve allowing for a quick and easy assembly and removal as well. The outer needle sleeve may comprise at least one bayonet slot including ramp sections that guide the cap arms during rotational movement of the cap with respect to the outer needle sleeve.

In an exemplary embodiment, the second locking mechanism comprises an audible and/or tactile feedback for indicating the release of the first locking mechanism to a user. For example, the bayonet slot comprises a protrusion, wherein the audible and/or tactile feedback will be generated when a cap drive member passes the protrusion and hits the ramp behind the protrusion.

In an exemplary embodiment, a spring is adapted to move the needle hub and the inner sleeve in the proximal direction with respect to the cartridge carrier when the first locking mechanism is released. The spring is coupled to the needle hub and the outer body, wherein a proximal end of the spring is coupled to the needle hub and a distal end of the spring is coupled to the outer needle sleeve.

In the initial state, the spring may bias the needle hub in the proximal direction. Thus, a release of the first locking mechanism causes a release of the spring. As a result, the needle hub and the inner sleeve are moved in the proximal direction with respect to the cartridge carrier. The spring may be configured as a compressible spring.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings, which are given by way of illustration only, and thus, are not limitative of the present disclosure, and wherein.

Corresponding parts are marked with the same reference symbols in all figures.

DETAILED DESCRIPTION

Figure 1:
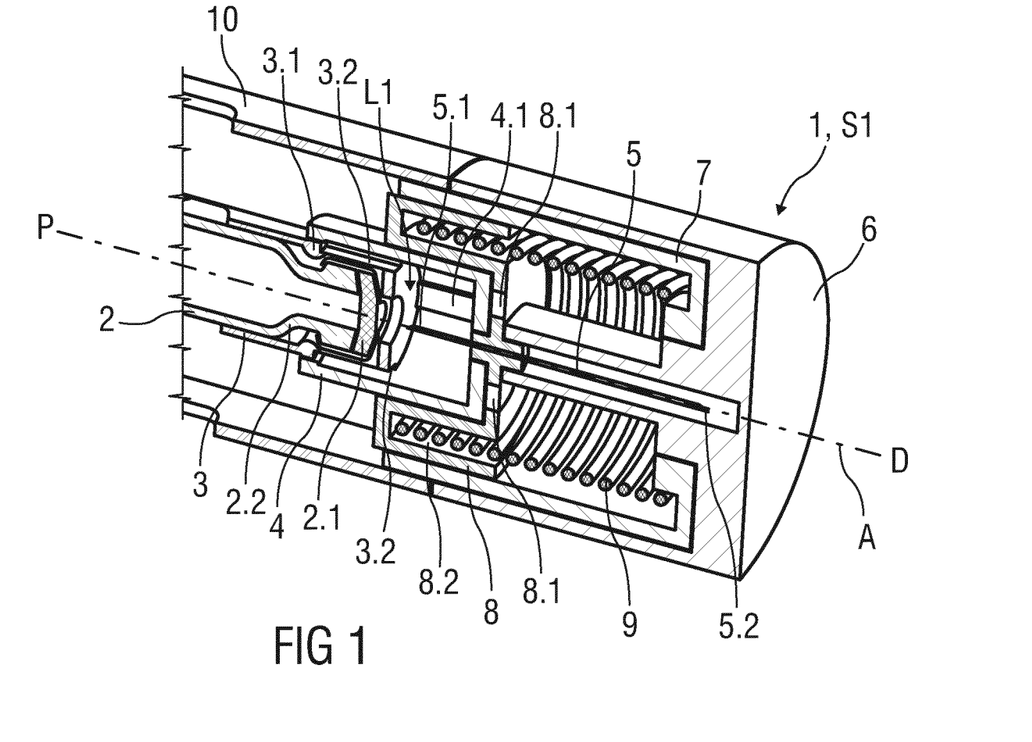
FIG. 1 is a schematic longitudinal detail section of an example of a drug delivery device in an initial state.

FIG. 1 shows a schematic longitudinal detail section of a drug delivery device 1 according to an exemplary embodiment of the present disclosure.

The drug delivery device 1 is in an initial state S1. In the context of the present application, the initial position P1 of the drug delivery device 1 is a position in which the drug delivery device 1 would be presented to the user prior to use before starting a drug delivery process.

The drug delivery device 1 comprises a cartridge 2 forming a cavity that contains a dosage of a medicament. The cartridge 2 comprises an open distal end which is sealed by a sealing element 2.1, e.g. a fluid impermeable membrane. Furthermore, a stopper (not shown) may be disposed within the cartridge 2 limiting the cavity of the cartridge 2 in a proximal direction P and adapted for displacing the medicament from the cartridge 2 during drug delivery.

The cartridge 2 is mounted in a substantially cylindrically shaped and hollow cartridge carrier 3, thereby radially fixed due to a cylindrical shape of bars (not shown) and axially fixed by an undercut that receives a cartridge crimp (not shown). The cartridge carrier 3 comprises a carrier rib 3.1 that is arranged proximally on an inner surface and protrudes in a radial inward direction in a manner to engage a shoulder portion 2.2 of the cartridge 2. The cartridge carrier 3 further comprises a number of recesses 3.2 arranged on an outer circumference of a distal portion. For example, the cartridge carrier 3 comprises two recesses 3.2 extending in parallel to a longitudinal axis A of the drug delivery device 1.

Figure 2:
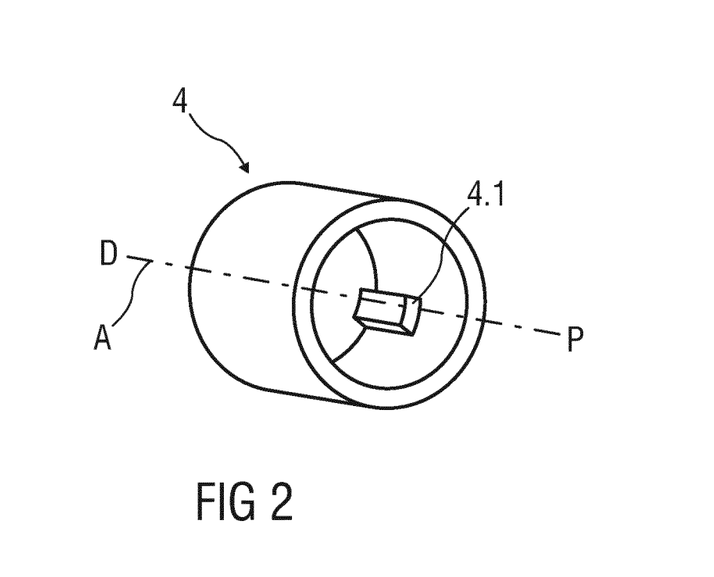
FIG. 2 is a schematic perspective view of an inner needle sleeve of the drug delivery device.

The recesses 3.2 are adapted to engage corresponding sleeve ribs 4.1 of an inner needle sleeve 4. The inner needle sleeve 4 is substantially cup-shaped and encloses at least the distal portion of the cartridge carrier 3. In the initial state S1 of the drug delivery device 1, a distal end of the cartridge carrier 3 bears against the sleeve ribs 4.1, wherein the recesses 3.2 are angularly misaligned from the sleeve ribs 4.1 and do thus not engage the sleeve ribs 4.1. The exemplary embodiment shown in FIGS. 1 and 2 illustrates one sleeve rib 4.1 respectively. Likewise, the inner needle sleeve 4 may comprise two or more sleeve ribs 4.1, wherein the number of recesses 3.2 is at least equal to the number of sleeve ribs 4.1.

Figure 3:
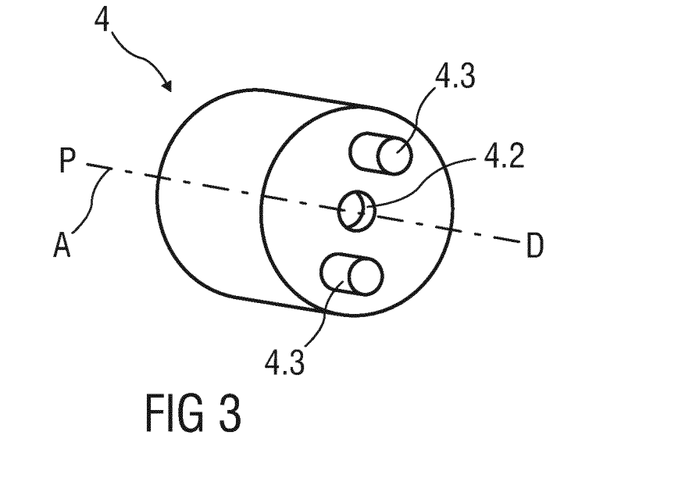
FIG. 3 is a schematic perspective view of the inner needle sleeve of the drug delivery device.

FIG. 2 shows the inner needle sleeve 4 in a schematic perspective. FIG. 3 shows the inner needle sleeve 4 in a further perspective view.

The illustrated sleeve rib 4.1 is arranged on an inner surface of the inner needle sleeve 4 and projects radially inwards. The sleeve rib 4.1 extends from a bottom end of the inner needle sleeve 4 in the proximal direction P by a certain length, but not up to the proximal end of the inner needle sleeve 4. The length of the sleeve rib 4.1 may correspond with the length of the recess 3.2. The bottom end of the inner needle sleeve 4 is a closed distal end comprising a central aperture 4.2 through which a double ended hollow needle 5 may pass. The inner needle sleeve 4 further comprises a number of sleeve pins 4.3 adapted to engage with a number of cap arms 6.1 of a cap 6 which will be described in more detail below. The sleeve pins 4.3 protrude axially from the distal end in the distal direction D as illustrated in FIG. 3. The inner needle sleeve 4 may comprise two sleeve pins 4.3 as illustrated in FIG. 3.

Referring again to FIG. 1, in the initial state S1, the inner needle sleeve 4 is locked against axial movement with respect to the cartridge carrier 3 by a first locking mechanism L1. The first locking mechanism comprises the sleeve ribs 4.1 and the recesses 3.2. As long as the sleeve ribs 4.1 are not engaged with the recesses 3.2, the cartridge carrier 3 bears against the sleeve ribs 4.1 and the inner needle sleeve 4 is thus not allowed to move in the proximal direction P with respect to the cartridge carrier 3.

The inner needle sleeve 4 is slidably arranged within an outer needle sleeve 7, whereby the inner needle sleeve 4 is locked against axial movement with respect to the outer needle sleeve 7 by the first locking mechanism L1. To guide a movement of the inner needle sleeve 4 with respect to the outer needle sleeve 7 when the first locking mechanism L1 is released, the outer needle sleeve 7 may comprise a section with a reduced inner diameter in which a part of the inner needle sleeve 4 is slidably arranged. Likewise, the inner needle sleeve 4 may comprise a projection on the outer circumference that is guided within a slot arranged on the inner circumference of the outer needle sleeve 7 or vice versa.

Figure 4:
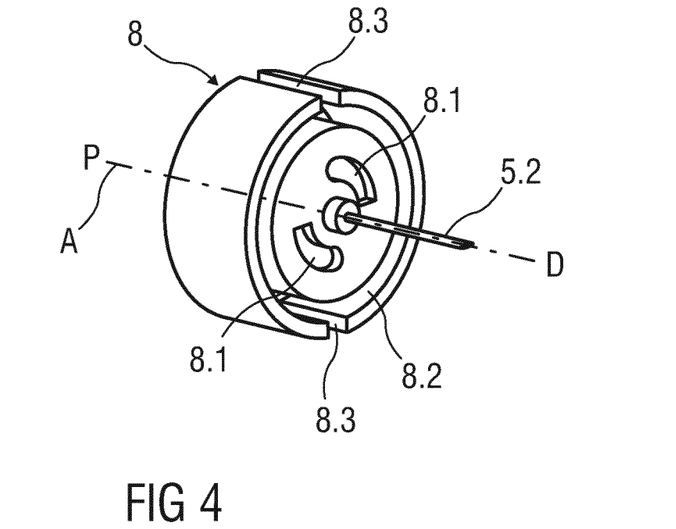
FIG. 4 is a schematic perspective view of a needle hub holding a double-ended hollow needle.

The inner needle sleeve 4 is coupled to a needle hub 8 that is shown in FIG. 4 in more detail, wherein FIG. 4 is a schematic perspective view of the needle hub 8.

The needle hub 8 comprises the needle 5 that is arranged through an aperture of a central stem. The needle 5 is thus divided into a proximal needle section 5.1 and a distal needle section 5.2 by the central stem.

The distal needle section 5.2 comprises a needle tip that is targeted outside the needle hub 8 in the distal direction D. The needle hub 8 is substantially cup-shaped and adapted to enclose a distal portion of the inner needle sleeve 4, wherein the distal end of the inner needle sleeve 4 bears against a bottom end of the needle hub 8. The aperture of the needle hub 8 and the central aperture 4.2 of the inner needle sleeve 4 are aligned to each other. Thus, the proximal needle section 5.1 passes through the central aperture 4.2 and comprises a needle tip that is targeted inside the inner needle sleeve 4 in the proximal direction P. In the initial state S1, the needle tip of the proximal needle section 5.1 is distally spaced from the cartridge 2 and the cartridge carrier 3 and is thus not in fluid communication with the medicament.

The bottom end of the needle hub 8 comprises two openings 8.1 configured as curved elongated holes. The openings 8.1 are adapted to receive the sleeve pins 4.3 which are guidable within the openings 8.1 by the cap arms 6.1, as described below.

Figure 6:
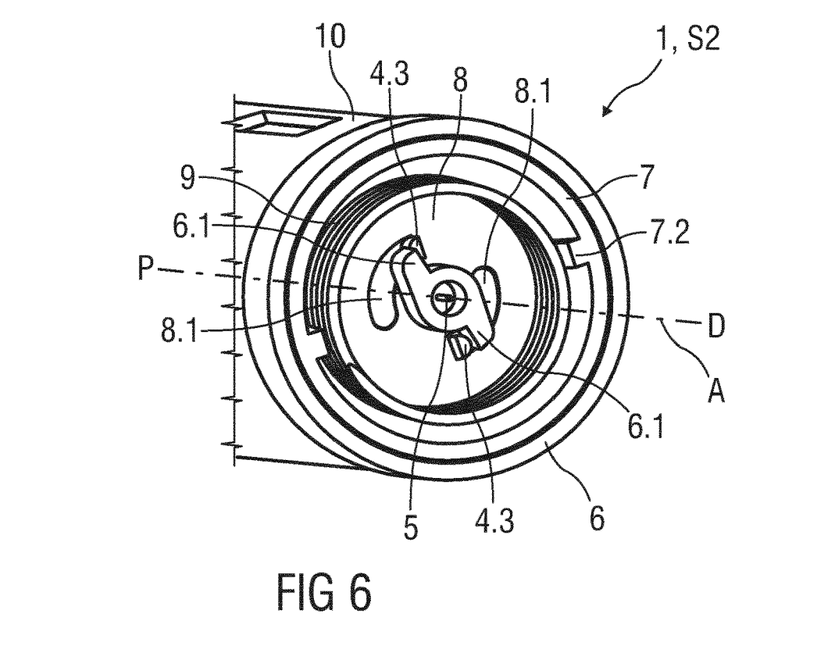
FIG. 6 is a schematic cross section of the drug delivery device with a released first locking mechanism.
Figure 7:
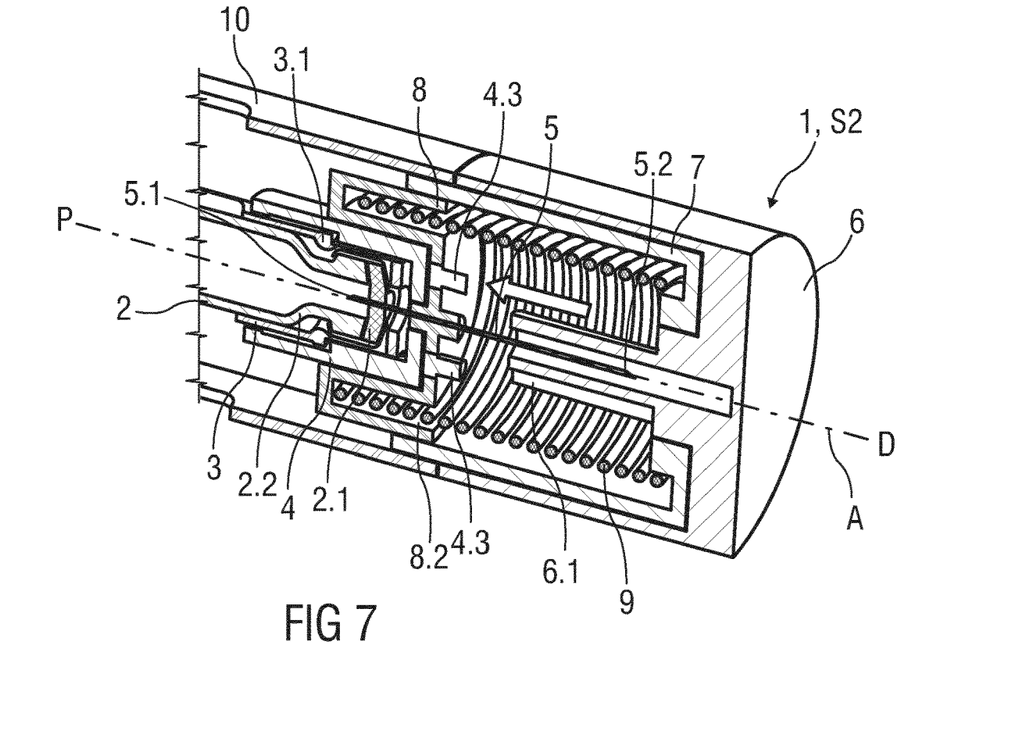
FIG. 7 is a schematic longitudinal detail section of the drug delivery device with the released first locking mechanism.

The needle hub 8 further comprises a circular slot 8.2 in which a proximal end of a compressible spring 9 is arranged. The spring 9 is adapted to drive the needle hub 8 and the inner needle sleeve 4 in the proximal direction P with respect to the cartridge carrier 3 when the first locking mechanism L1 is released as illustrated in FIGS. 6 and 7. Thereby, the spring 9 biases the needle hub 8 in the proximal direction P. The spring 9 is further coupled to the outer needle sleeve 7 with a distal end and thus additionally adapted to move the outer needle sleeve 7 in the distal direction D with respect to the needle hub 8 to cover the needle tip of the distal needle section 5.2 after the drug delivery device 1 is removed from an injection site.

Figure 5:
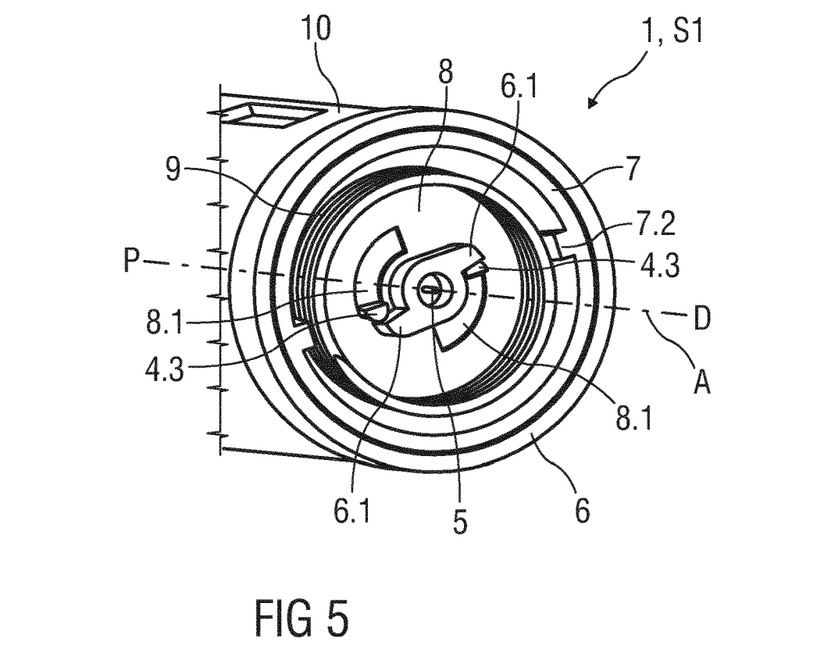
FIG. 5 is a schematic cross section of the drug delivery device in the initial state.

Referring to the exemplary embodiment of the needle hub 8 shown in FIG. 4, the needle hub 8 further comprises two guiding slots 8.3 adapted to guide an axial movement of the needle hub 8 within the outer needle sleeve 7. The outer needle sleeve 7 comprises corresponding guiding protrusions 7.2 engaging the guiding slots 8.3 as illustrated in FIG. 5.

The distal needle tip 5.2 is sealed and secured against environmental influences by the cap 6 that is coupled to the outer needle sleeve 7 and to an outer body 10 which partially encloses the outer needle sleeve 7. In the initial state S1, the outer needle sleeve 7 projects beyond the outer body 10 in the distal direction D. The projecting section of the outer needle sleeve 7 is enclosed by the cap 6.

Figure 8:
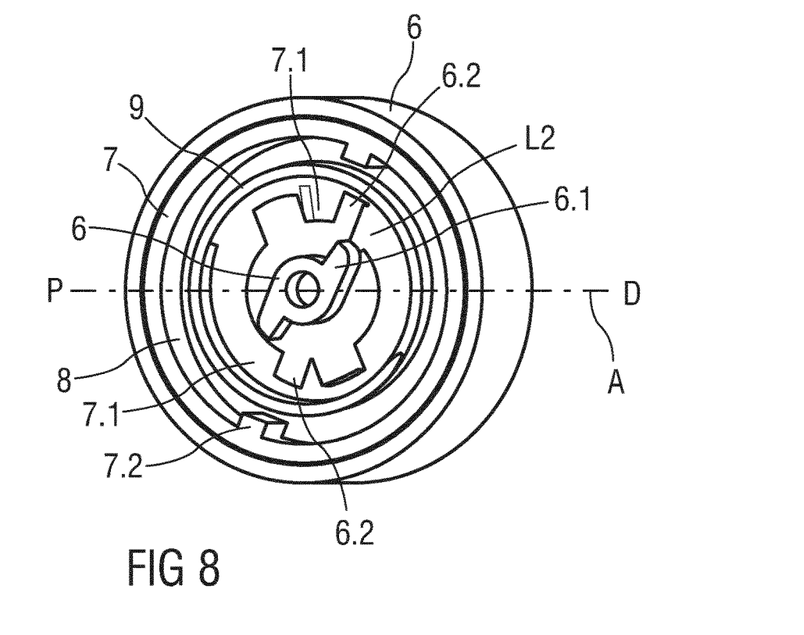
FIG. 8 is a schematic cross section of the drug delivery device.

The cap 6 is locked to the outer needle sleeve 7 by a second locking mechanism L2 which is adapted to prevent an unintended removal of the cap 6 before the first locking mechanism L1 is released. The second locking mechanism L2 may be configured as a bayonet connection. To this end, the outer needle sleeve 7 may comprise at least one bayonet slot 7.1 that is at least section-wise configured as a ramp for guiding a cap drive member 6.2 of the bayonet connection as illustrated in FIG. 8 in order to provide a tactile feedback to the user when the cap 6 is completely turned and the first locking mechanism L1 is released.

The cap 6 comprises the cap arms 6.1 as mentioned above. For example, the cap 6 comprises two cap arms 6.1. The cap arms 6.1 are arranged on an outer circumference of a central stem configured as a hollow stem for receiving the distal needle section 5.2. The stem projects into the cap 6 in the proximal direction P. The cap arms 6.1 project radially outwards from the outer circumference of the stem. For example, the cap arms 6.1 extend along a longitudinal extension of the stem in parallel to the longitudinal axis A. The cap arms 6.1 are adapted to engage the sleeve pins 4.3 by angularly abutting the sleeve pins 4.3. In the initial state S1, the sleeve pins 4.3 are arranged on one end of the openings 8.1 respectively as illustrated in FIG. 5.

FIG. 5 shows a cross section of the drug delivery device 1 in the initial state S1.

In order to perform a drug delivery process, the drug delivery device 1 may be activated as described in the following FIGS. 6 to 8.

FIG. 6 shows a cross section of the drug delivery device 1 in an activating state S2.

The cap 6 has been rotated around the longitudinal axis A with respect to the outer sleeve 7 and the outer body 10. Compared to FIG. 5, the cap 6 has been rotated around the longitudinal axis A at an angle of 90 degrees. In a not shown alternative embodiment, the cap 6 may be rotated at an angle of more or less than 90 degrees.

Due to the engagement of the cap arms 6.1 and the sleeve pins 4.3, the inner needle sleeve 4 rotates with respect to the needle hub 8 and the cartridge carrier 3, following the rotational movement of the needle cap 6 until the sleeve pins 4.3 abut against the other ends of the openings 8.1 respectively. As the inner needle sleeve 4 rotates with respect to the cartridge carrier 3, the recesses 3.2 engage the sleeve ribs 4.1.

The first locking mechanism L1 is now released allowing the inner needle sleeve 4 to move axially with respect to the cartridge carrier 3. Consequently, the compressed spring 9 relaxes and pushes the needle hub 8 and the inner needle sleeve 4 in the proximal direction P with respect to the cartridge carrier 3 until the bottom end of the inner needle sleeve 4 abuts against the distal end of the cartridge carrier 3. During the axial movement of the needle hub 8 and the inner needle sleeve 4, the needle tip of the proximal needle section 5.1 passes through the open distal end of the cartridge carrier 3 and pierces the sealing element 2.1. Thus, the needle 5 gets in fluid communication with the medicament stored in the cartridge 2.

FIG. 7 shows a longitudinal section of the drug delivery device 1 in the activating state S2 with a released locking mechanism L1.

Due to the bayonet connection between the cap 6 and the outer needle sleeve 7, the second locking mechanism L2 can be released after the first locking mechanism L1 is released. The cap 6 is then allowed to be removed by pulling the cap 6 off the outer needle sleeve 7.

FIG. 8 shows a schematic cross section of the drug delivery device 1.

The bayonet slot 7.1, in particular the section configured as a ramp may comprise a protrusion (not shown) adapted to provide a tactile feedback indicating to a user that the first locking mechanism L1 is released. The audible feedback will be generated when the cap drive member 6.2 passes the protrusion and hits the bayonet slot 7.1 behind the protrusion. The cap arms 6.2 are designed in such a manner that a release force is adjustable due to a height difference of the ramp section of the bayonet slot 7.1 and the mechanical flexibility of the cap arms 6.2.

A drug delivery device 1 as it is described above may be suitable for use as a pen-type device with an automatic needle insertion and/or an automatic medicament delivery.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof.

Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 drug delivery device
2 cartridge
2.1 sealing element
2.2 shoulder portion
3 cartridge carrier
3.1 carrier rib
3.2 recess
4 inner needle sleeve
4.1 sleeve rib
4.2 central aperture
4.3 sleeve pin
5 needle
5.1 proximal needle section
5.2 distal needle section
6 cap
6.1 cap arm
6.2 cap drive member
7 outer needle sleeve
7.1 bayonet slot
7.2 guiding protrusions
8 needle hub
8.1 opening
8.2 slot
8.3 guiding slot
9 spring
10 outer body
A longitudinal axis
D distal direction
P proximal direction
L1 first locking mechanism
L2 second locking mechanism
S1 initial state
S2 activating state

The invention claimed is:
1. A drug delivery device comprising:
an outer needle sleeve;
a cartridge containing a dosage of a medicament, the cartridge sealed with a sealing element that is arranged across an open distal end of the cartridge;
a cartridge carrier adapted to hold the cartridge;
a needle hub adapted to hold a double ended hollow needle;
an inner needle sleeve arranged between the needle hub and the cartridge carrier;
a removable cap coupled to the inner needle sleeve and adapted to cover and seal the needle; and a first locking mechanism adapted to lock the inner needle sleeve against axial movement in a proximal direction with respect to the cartridge carrier when the drug delivery device is in an initial state, wherein the first locking mechanism is arranged between the inner needle sleeve and the cartridge carrier, wherein, when the drug delivery device is in the initial state, the needle is spaced from the cartridge in a distal direction, wherein the first locking mechanism is releasable by a rotational movement of the cap with respect to the outer needle sleeve, and wherein the first locking mechanism comprises:
one or more recesses arranged in an outer circumference of a distal portion of the cartridge carrier; and
one or more sleeve ribs arranged on an inner circumference of the inner needle sleeve and projecting radially inwards.

2. The drug delivery device according to claim 1, wherein an angle of the rotational movement of the cap with respect to the outer needle sleeve is in a range of 30 degrees to 45 degrees.

3. The drug delivery device according to claim 1, wherein an angle of the rotational movement of the cap with respect to the outer needle sleeve is in a range of 30 degrees to 90 degrees.

4. The drug delivery device according to claim 1, wherein an angle of the rotational movement of the cap with respect to the outer needle sleeve is more than 90 degrees.

5. The drug delivery device according to claim 1, wherein, when the drug delivery device is in the initial state, a distal end of the cartridge carrier couples to the one or more sleeve ribs, and wherein the one or more recesses are angularly misaligned from the one or more sleeve ribs.

6. The drug delivery device according to claim 1, wherein the first locking mechanism is released when the one or more sleeve ribs engage into the one or more recesses, such that the needle hub and the inner needle sleeve move in the proximal direction with respect to the cartridge carrier.

7. The drug delivery device according to claim 1, wherein a second locking mechanism is adapted to lock the cap against axial removal from the outer needle sleeve.

8. The drug delivery device according to claim 7, wherein the second locking mechanism is releasable when the first locking mechanism is released.

9. The drug delivery device according to claim 7, wherein the second locking mechanism includes a bayonet connection between the cap and the outer needle sleeve.

10. The drug delivery device according to claim 9, wherein the outer needle sleeve comprises at least one bayonet slot having ramp sections that guide a plurality of cap arms of the cap during rotational movement of the cap with respect to the outer needle sleeve.

11. The drug delivery device according to claim 7, wherein the second locking mechanism comprises at least one of an audible feedback or a tactile feedback for indicating to a user a release of the first locking mechanism.

12. The drug delivery device according to claim 1, wherein a spring is adapted to move the needle hub and the inner needle sleeve in the proximal direction with respect to the cartridge carrier when the first locking mechanism is released.

13. The drug delivery device according to claim 12, wherein a proximal end of the spring is coupled to the needle hub and a distal end of the spring is coupled to the outer needle sleeve.

14. The drug delivery device according to claim 1, wherein the spring biases the needle hub in the proximal direction when the drug delivery device is in the initial state.

15. A drug delivery device comprising:
an outer needle sleeve;
a cartridge containing a dosage of a medicament, the cartridge sealed with a sealing element that is arranged across an open distal end of the cartridge;
a cartridge carrier adapted to hold the cartridge;
a needle hub adapted to hold a double ended hollow needle;
an inner needle sleeve arranged between the needle hub and the cartridge carrier;
a removable cap coupled to the inner needle sleeve and adapted to cover and seal the needle; and
a first locking mechanism adapted to lock the inner needle sleeve against axial movement in a proximal direction with respect to the cartridge carrier when the drug delivery device is in an initial state,
wherein the first locking mechanism comprises parts of the inner needle sleeve and the cartridge carrier,
wherein, when the drug delivery device is in the initial state, the needle is spaced from the cartridge in a distal direction,
wherein the first locking mechanism is releasable by a rotational movement of the cap with respect to the outer needle sleeve,
wherein the inner needle sleeve comprises a plurality of sleeve pins on a distal end projecting axially in a distal direction,
the cap comprises a plurality of cap arms projecting axially in a proximal direction and engaging the plurality of sleeve pins, and
wherein the needle hub comprises a plurality of openings through which the plurality of sleeve pins project.

* * * * *

UNITED STATES PATENT AND TRADEMARK OFFICE
CERTIFICATE OF CORRECTION

PATENT NO. : 10,549,039 B2  
APPLICATION NO. : 15/736627  
DATED : February 4, 2020  
INVENTOR(S) : Michael Helmer Page 1 of 1

It is certified that error appears in the above-identified patent and that said Letters Patent is hereby corrected as shown below:

In the Specification

In Column 1, Line 10 (approx.), delete "contends" and insert -- contents --

Signed and Sealed this  
Sixth Day of October, 2020

Andrei Iancu  
*Director of the United States Patent and Trademark Office*